United States Patent
Vitullo et al.

(10) Patent No.: US 10,398,877 B2
(45) Date of Patent: Sep. 3, 2019

(54) SYSTEM AND METHOD FOR INSERTING A CATHETER

(71) Applicants: Jeff Vitullo, Pottstown, PA (US); Bill Vojtasek, Wyomissing, PA (US)

(72) Inventors: Jeff Vitullo, Pottstown, PA (US); Bill Vojtasek, Wyomissing, PA (US)

(*) Notice: Subject to any disclaimer, the term of this patent is extended or adjusted under 35 U.S.C. 154(b) by 745 days.

(21) Appl. No.: 14/705,625

(22) Filed: May 6, 2015

(65) Prior Publication Data
US 2015/0320977 A1 Nov. 12, 2015

Related U.S. Application Data

(60) Provisional application No. 61/989,048, filed on May 6, 2014.

(51) Int. Cl.
| | |
|---|---|
| *A61M 25/01* | (2006.01) |
| *A61M 25/06* | (2006.01) |
| *A61M 25/00* | (2006.01) |
| *A61M 25/09* | (2006.01) |

(52) U.S. Cl.
CPC .... *A61M 25/0113* (2013.01); *A61M 25/0041* (2013.01); *A61M 25/01* (2013.01); *A61M 25/0102* (2013.01); *A61M 25/0606* (2013.01); *A61M 25/09041* (2013.01); *A61M 25/09016* (2013.01); *A61M 2025/0008* (2013.01); *A61M 2025/0063* (2013.01); *A61M 2025/0183* (2013.01); *A61M 2025/09058* (2013.01); *A61M 2025/09116* (2013.01)

(58) Field of Classification Search
CPC ....... A61B 5/6851; A61M 2025/09116; A61M 2025/09125; A61M 25/0293; A61M 2025/0063; A61M 2025/0177; A61M 25/0113; A61M 25/0041; A61M 25/0102; A61M 25/0606; A61M 25/0941
See application file for complete search history.

(56) References Cited

U.S. PATENT DOCUMENTS

| | | | | |
|---|---|---|---|---|
| 5,031,636 | A | * | 7/1991 | Gambale ........... A61M 25/0169 600/585 |
| 5,324,269 | A | * | 6/1994 | Miraki ................ A61M 25/104 604/160 |
| 5,382,238 | A | * | 1/1995 | Abrahamson ..... A61M 25/0102 600/434 |

(Continued)

*Primary Examiner* — Laura A Bouchelle
*Assistant Examiner* — Melissa A Snyder
(74) *Attorney, Agent, or Firm* — Patnstr, APC; Peter Jon Gluck

(57) ABSTRACT

The invention provides methods and systems for introducing a catheter into a blood vessel. A catheter set comprising a pre-loaded stylet in a catheter is connectable to a guidewire. The guidewire may be introduced into the patient through a hollow needle. The stylet can then be connected to the guidewire, and the catheter advanced over the stylet and the guidewire into the access site and into position in the blood vessel of the patient. The invention reduces the time and placement steps required to position a catheter in a vessel and lowers the associated procedural costs. The invention reduces the frequency and severity of complications generally associated with introducing a catheter, thereby improving patient outcomes and lowering healthcare costs.

14 Claims, 8 Drawing Sheets

(56) References Cited

U.S. PATENT DOCUMENTS

| | | | | |
|---|---|---|---|---|
| 5,584,803 A | * | 12/1996 | Stevens | A61B 17/29 604/101.01 |
| 8,083,728 B2 | * | 12/2011 | Rome | A61M 39/06 604/167.03 |
| 2008/0281228 A1 | * | 11/2008 | Parodi | A61M 25/09 600/585 |

* cited by examiner

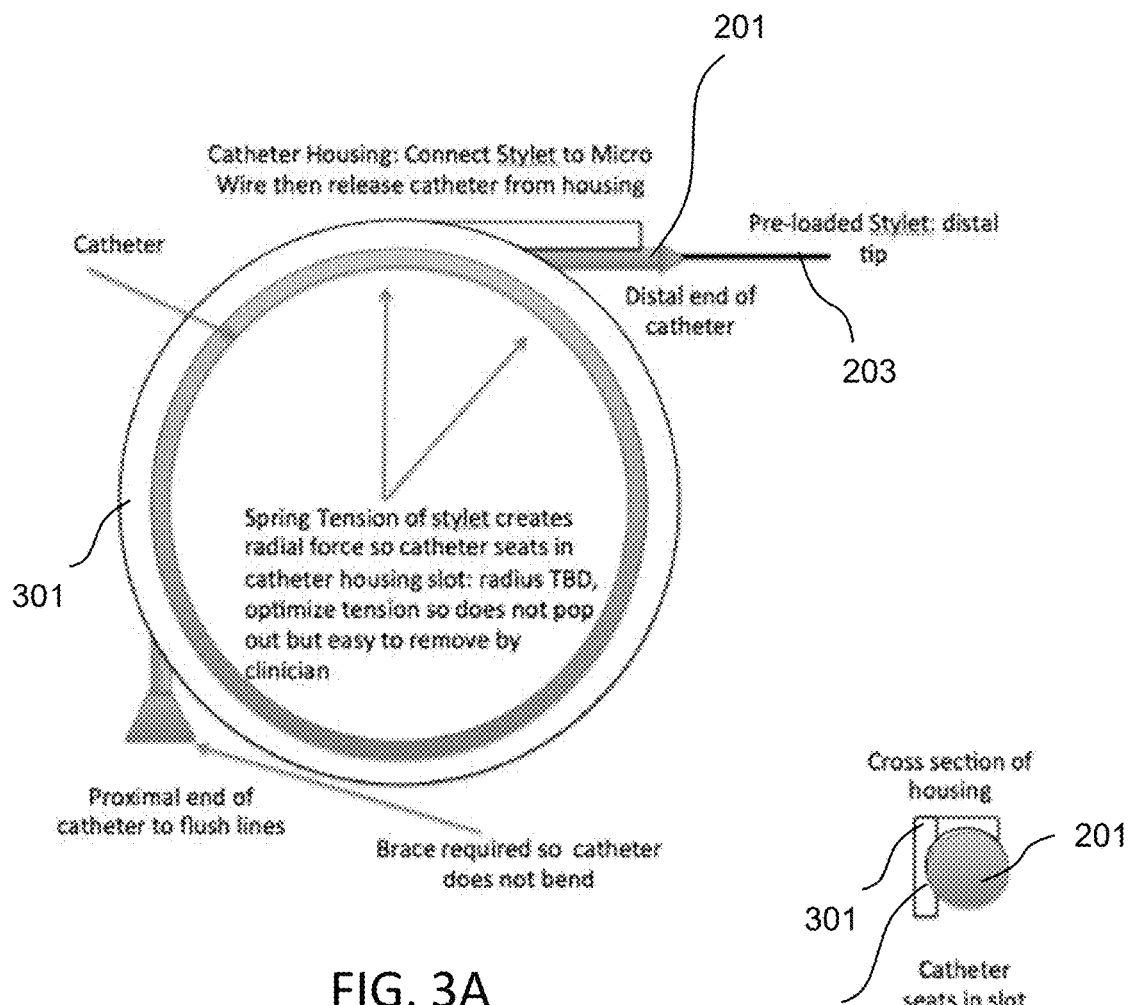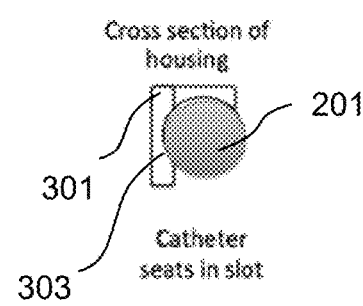
FIG. 3A
FIG. 3B

Connection means:

Stylet                          Guidewire 5 lb min coupling force 203    213
            211

SECTION A-A

SYSTEM AND METHOD FOR INSERTING A CATHETER

RELATED APPLICATIONS

This application claims priority to and the benefit of U.S. provisional application Ser. No. 61/989,048, filed May 6, 2014, the content of which is incorporated by reference herein in its entirety.

FIELD OF THE INVENTION

The invention relates to systems and methods for inserting a catheter into the body.

BACKGROUND

Introducing a catheter into the vasculature is a common medical technique, but one that is prone to severe complications. To insert a catheter, an access site (i.e., an incision) must be made in an arterial wall. Traditionally, a catheter is introduced using the Seldinger technique, named for a Swedish radiologist who invented the procedure in 1953. In the Seldinger technique, a blood vessel is punctured with a hollow needle. Venous placement is confirmed by monitoring pulsatile blood flow through the needle. When that flow of blood confirms that the needle has accessed the vessel, a round-tipped guidewire is advanced through the lumen of the needle into the vessel. The guidewire is held in place while the needle is withdrawn. Generally the cutaneous puncture site is widened with a scalpel to create a larger hole for the catheter to pass through. A dilator may be used to enlarge the access site as needed. Next a catheter sheath is threaded onto the guidewire. The catheter is passed over the guidewire using a twisting motion to advance it into the vessel, and the catheter is advanced to its final indwelling position. The guidewire is then withdrawn through the catheter, leaving the catheter in place in the vessel.

The Seldinger technique involves several moving parts and placement steps. Each step requires time and precision, and each part must be sterile to avoid infection to the patient. Thus, many risks are involved. For example, complications may arise when a part is withdrawn prematurely, for example the guidewire being inadvertently pulled out with the needle. Alternatively, guidewire embolism can occur when the guidewire gets lost in the vein while the clinician is pushing the dilator or the sheath over it. Creating a suitable access site often involves multiple attempts, each with an associated risk of vein puncture and hematoma. Access site complications are the most common type of complication after diagnostic and percutaneous coronary intervention, and complication rates are even higher for procedures involving large arterial sheaths for device delivery such as in aortic valve replacement. Frequent complications include air embolism, bloodstream infection, bleeding, contamination, and loss of cannulation. Those complications increase patient morbidity and mortality, lengthen hospital stays, and increase healthcare costs.

SUMMARY

The invention provides a simpler and quicker method for introducing a catheter into a blood vessel. The invention provides a pre-loaded stylet in a catheter, which is connectable to a guidewire. The guidewire may be introduced into the patient through a hollow needle. The stylet can then be connected to the guidewire, and the catheter advanced over the stylet and the guidewire into the access site and into position in the blood vessel of the patient. The invention allows a shorter guidewire, which reduces the sterile field zone required to accommodate longer guidewires, thus avoiding contamination. The catheter and stylet can be provided as a single unit, which can remain sealed and sterile during the time that the guidewire is being introduced to the access site. The stylet and guidewire can be connected quickly and easily. Methods of the invention reduce the time and placement steps required to position a catheter in a vessel, and lower the associated procedural costs. Additionally, the invention allows a catheter to be inserted using a smaller gauge needle, which reduces the complications associated with larger puncture sites. By reducing the frequency of complications, the invention improves patient outcomes, decreases mortality and morbidity, and lowers healthcare costs.

In general, methods of the invention involve accessing a vessel with an introducer needle or trocar. The needle can be a standard needle as used in a Seldinger or micropuncture technique. A guidewire is fed through the needle and advanced to a desired position. The needle is then removed over the guidewire. A catheter is provided that has a stylet pre-loaded. The stylet is configured so that it extends past the tip of the catheter by some length, for example 3 or more centimeters. The stylet extends through the catheter and the catheter extension line. The proximal end of the stylet is connected to the catheter extension line luer by means of a cap. The cap is flushable so that the catheter lumen can be primed with the stylet in place. The catheter and stylet can be provided in a catheter housing, in which the catheter and stylet can coil up and fit circumferentially. The catheter and stylet can remain in the housing until the distal end of the stylet is connected to the proximal end of the guidewire.

In certain aspects, the invention provides a method for introducing a catheter into a blood vessel. The method includes inserting a hollow needle into a blood vessel and feeding a guidewire, having a proximal end and a distal end, through the needle. The method further involves removing the needle from the blood vessel, leaving the guidewire therein. The method further involves providing a catheter set that includes a catheter having a proximal end and a distal end and defining a lumen; and a stylet having a proximal end and a distal end, wherein the stylet is disposed within the catheter lumen, and wherein the distal end of the stylet extends out of the distal end of the catheter. The method further involves connecting the distal end of the stylet to the proximal end of the guidewire to create a stylet-guidewire complex, advancing the catheter into the vessel over the stylet-guidewire complex, and withdrawing the stylet-guidewire complex, thereby having introduced the catheter into the blood vessel in a desired location.

In certain embodiments, the hollow needle may define a needle lumen extending axially therethrough, and the needle lumen may have a diameter greater than a diameter of the stylet. The guidewire may be between 15 and 20 cm in length, and may be between 0.018 inches and 0.035 inches in diameter, and the stylet may have a diameter equal to or greater than the diameter of the guidewire. The guidewire may comprise markings to indicate distance inserted, and it may include a J-tip or a floppy tip.

In embodiments, the catheter set may also include a catheter extension line and a luer, and the proximal end of the stylet may be secured to the luer. The method may further involve disconnecting the proximal end of the stylet from the luer prior to advancing the catheter into the vessel over the stylet-guidewire complex. The proximal end of the stylet may be secured to the luer with a cap. In some embodiments, the method may further involve flushing the catheter with a fluid prior to connecting the distal end of the stylet to the proximal end of the guidewire, with the cap still in place.

In some embodiments, the stylet extends at least 3 cm past the distal end of the catheter. The stylet may comprise a solid flexible material or a metal coil.

In certain aspects, the invention involves a system for introducing a catheter into a blood vessel. The system includes a guidewire and a catheter set. The guidewire is configured to be fed into a blood vessel through a hollow needle. The catheter set includes a catheter, having a proximal end and a distal end and defining a lumen, and a stylet having a proximal end and a distal end, wherein the stylet is disposed within the catheter lumen, and wherein the distal end of the stylet extends out of the distal end of the catheter. The distal end of the stylet is configured to be connectable to the proximal end of the guidewire to create a stylet-guidewire complex. The catheter is configured to be advanceable over the stylet-guidewire complex. The stylet-guidewire complex is configured to then be withdrawn from the vessel, thereby leaving the catheter in place in the blood vessel.

In certain embodiments, the hollow needle may define a needle lumen extending axially therethrough, and the needle lumen may have a diameter greater than a diameter of the stylet. The guidewire may be between 15 and 20 cm in length, and may be between 0.018 inches and 0.035 inches in diameter, and the stylet may have a diameter equal to or greater than the diameter of the guidewire. The guidewire may comprise markings to indicate distance inserted, and it may include a J-tip or a floppy tip.

In embodiments, the catheter set may also include a catheter extension line and a luer, and the proximal end of the stylet may be secured to the luer. The proximal end of the stylet may be secured to the luer with a cap. In some embodiments, the stylet extends at least 3 cm past the distal end of the catheter. The stylet may comprise a solid flexible material or a metal coil.

BRIEF DESCRIPTION OF THE DRAWINGS

FIGS. 3A and 3B show two views of a catheter housing for use with the invention.

DETAILED DESCRIPTION

The invention provides methods and systems for introducing a catheter into a blood vessel of a human or other animal having a vasculature.

The invention provides a catheter that can be placed into a blood vessel or other body lumen, such as via the femoral artery or the abdomen. The catheter may be a central venous catheter, a hemodialysis catheter, a peripheral catheter, or the like.

Figure 1:
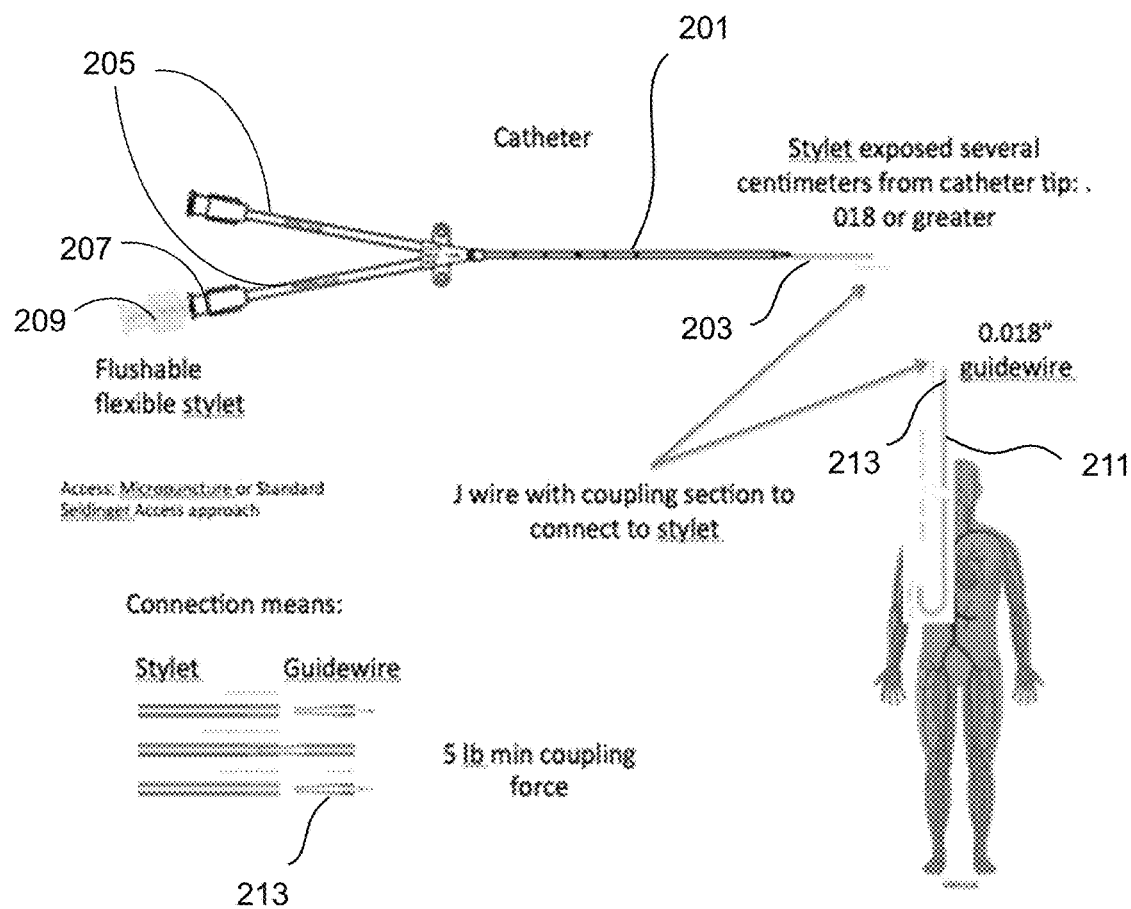
FIG. 1 shows a diagram of a system of the invention.

FIG. 1 shows a schematic diagram of a system of the invention. A catheter 201 has a lumen through which a stylet 203 is disposed. The stylet 203 comes pre-loaded in the catheter 201, and the whole unit can be contained in a sterile packaging, such as a sterile sock, to make a complete sterile field. The stylet 203 extends several centimeters from the distal end of the catheter 201. The stylet 203 may extend at least 1 mm, and up to a meter. Preferably, the stylet 203 extends between 1 and 10 cm past the distal tip of the catheter 201, and more preferably about 3 cm. The stylet 203 may comprise a solid flexible shaft or a coiled structure. It may be constructed from metal, plastic, polymer, or any other biocompatible material. The catheter 201 may comprise one or more catheter extension lines 205, each having a luer connector 207, such as a luer-lock, luer-slip, other suitable slip tip style connector. The stylet 203 connects to the luer 207 by a cap X. The cap 209 is flushable so that the catheter 201 can be primed before use with the stylet 203 remaining in place. The cap 209 can be disconnected by a user during use when the catheter 201 and the stylet 203 are to be disconnected.

The catheter is a cannula or tube. It is generally made of a resilient biocompatible polymer, and the luer ports allow attachment of an IV tube or provide access for laproscopic surgical devices.

A guidewire 211 is introduced into the blood vessel of a patient by a hollow needle or trocar (not shown). The needle can be any hollow needle known in the art for introducing a guidewire into a body lumen. The present invention allows narrow guidewires, for example 0.035-inch guidewires or less, and preferably guidewires having a diameter of 0.018 inches or less. The guidewire 211 can be between 5 and 100 cm in length, but preferably about 15 to 20 cm in length. The guidewire 211 may comprise cm markings to indicate the distance it has been advanced. The guidewire 211 as shown has a J-tip at the distal (interior) end and a coupling section 213 at its proximal (exterior) end. The coupling section 213 connects to the distal end of the stylet by a coupling means (shown in greater detail in FIGS. 4 and 5). Once connected, the stylet 203 and the guidewire 211 form a continuous stylet-guidewire complex or tract, over which the catheter 201 can be advanced into the vessel. Once the catheter 201 is inserted into the desired location, the entire tract can be removed and discarded.

The system of the present invention is compatible with EKG guidance for verification of terminal tip position. EKG-guided peripherally inserted central catheters are known to be accurate without x-ray confirmation in consistently guiding the terminal tip to the superior vena cava, for example. Use of EKG prevents patient exposure to radiation and saves time.

Figure 2:
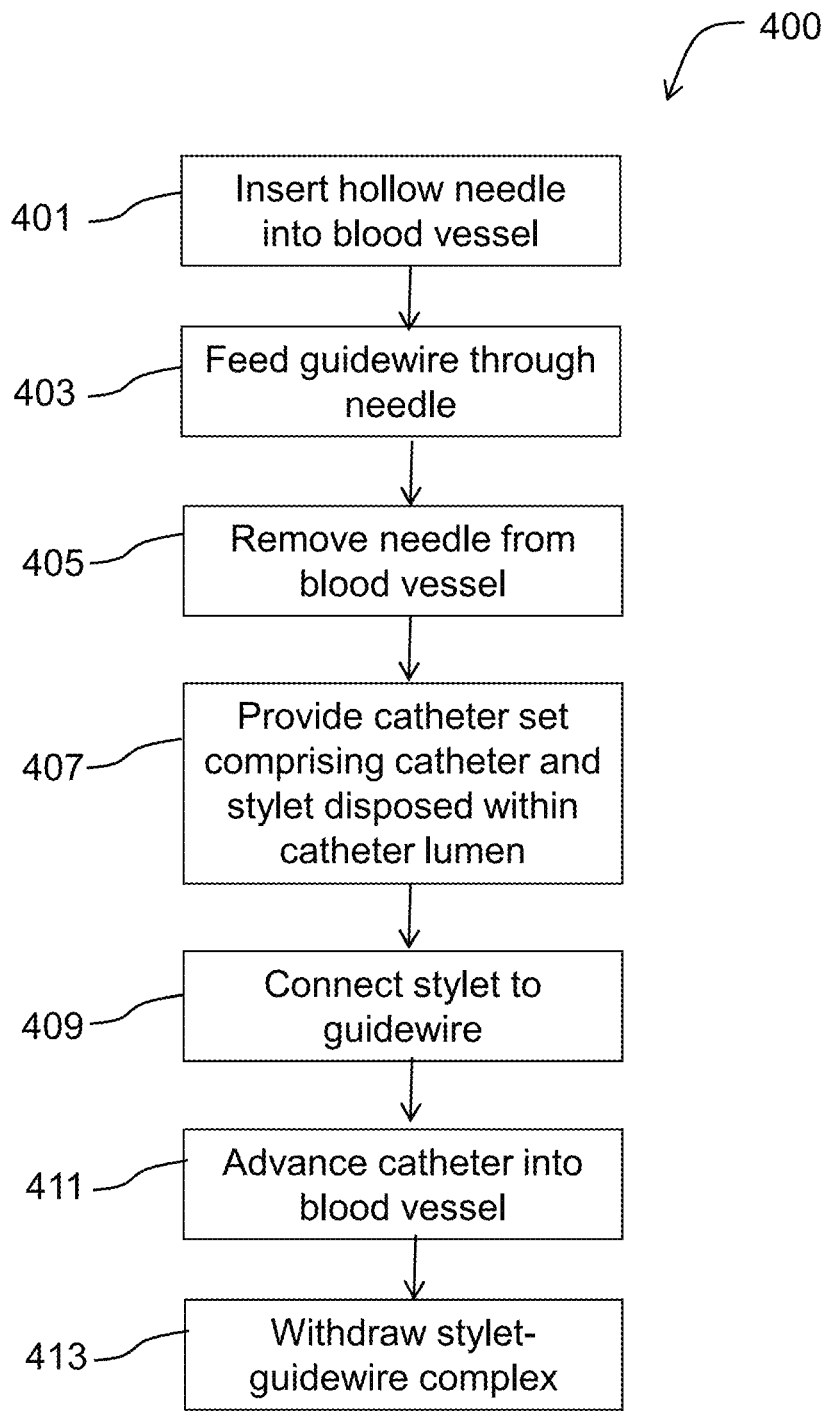
FIG. 2 shows a flowchart of a method of the invention.

FIG. 2 sows a flow chart of a method 400 for introducing a catheter into a blood vessel, according to the invention. According to the method 400, a hollow needle is inserted 401 into a blood vessel. Then a guidewire is fed 403 through the needle. The needle is then removed 405 from the blood vessel, leaving the guidewire therein. Next a catheter set is provided 407, the set including a catheter and a stylet. The stylet is disposed within a lumen of the catheter, such that the distal end of the stylet extends out of the distal end of the catheter. The distal end of the stylet is connected 409 to the proximal end of the guidewire to create a stylet-guidewire complex, and the catheter is advanced 411 into the vessel over the stylet-guidewire complex. Finally, the stylet-guidewire complex is withdrawn 413, thereby having introduced the catheter into the blood vessel in a desired location.

FIG. 3A shows a catheter housing 301 for use with the invention. The circumferential housing 301 has a slot 303 (shown in cross-section in FIG. 3B). The housing 301 is designed to hold the catheter 201 and stylet 203 in a circular pattern to minimize profile and preserve functionality of the system. In operation, the stylet 203 is connected to the guidewire 211 at the guidewire's distal end 213. The catheter 201 can then be released from the housing 301. The spring tension of the stylet 203 creates a radial force so that the catheter 201 remains seated in the slot 303. The radius of the housing 301 can be between 4 cm and 20 cm, but in any event is designed to optimize tension so that the catheter 201 remains seated in the slot 303, but is easy to remove by a clinician. The housing creates protects the catheter and helps create a sterile environment before the catheter 201 is in use and while the stylet 203 is being connected to the guidewire.

Figure 4:
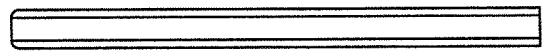
FIG. 4 shows a close-up view of the connection between the stylet and the guidewire.
Figure 4:
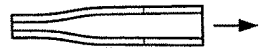
Figure 4:
Figure 4:
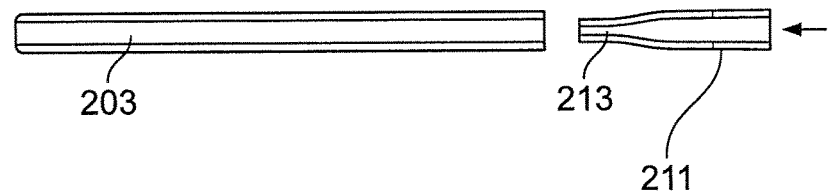

FIG. 4 shows a configuration of how the stylet 203 can be connected and disconnected from the guidewire 211. In the embodiment shown, the guidewire has a tapered coupling section 213 at its proximal end. The coupling section is tapered so that it fits within a lumen at the distal end of the stylet 203. The guidewire 211 and stylet 203 are both made of resilient biocompatible materials, such that upon insertion of the coupling section 213, at least 5 lbs. of coupling force is exerted holding the two pieces together, due to the friction between the outer surface of the coupling section 213 and the inner surface of the stylet lumen. The coupling force is sufficient to prevent the guidewire 211 from decoupling and being lost inside the vasculature during operation. However, it is not so great that a clinician is unable to pull the pieces apart as necessary.

Figure 5:
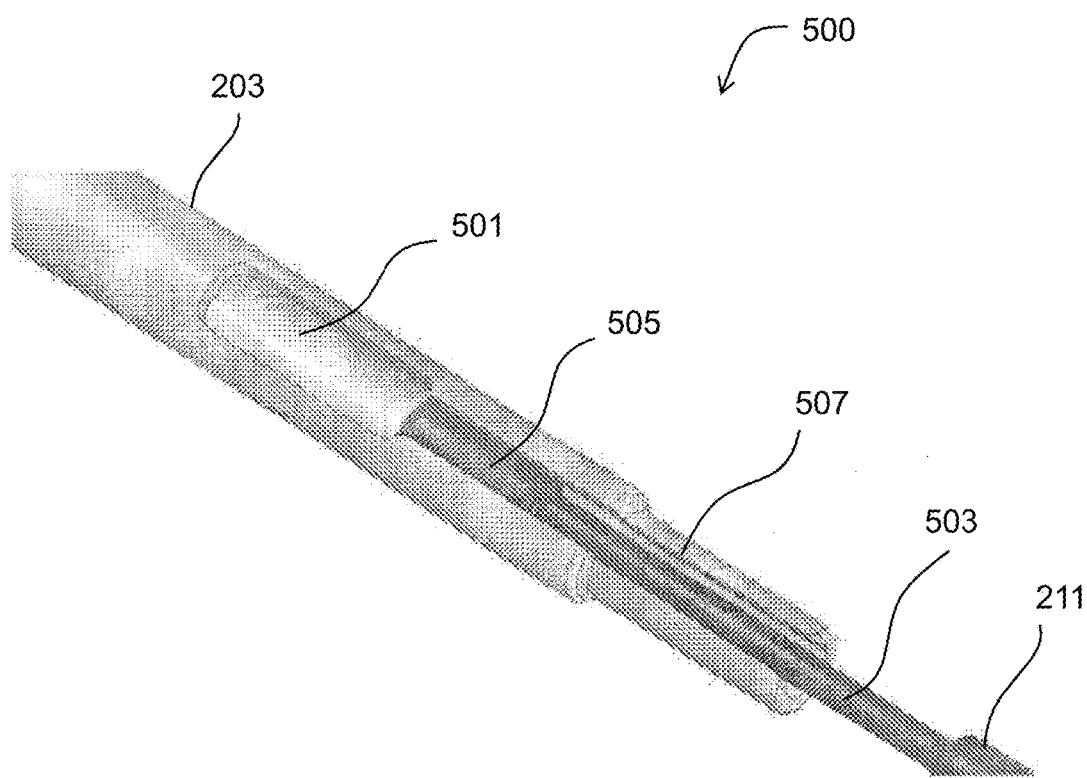
FIG. 5 shows a close-up view of the another embodiment of the connection between the stylet and the guidewire.

FIG. 5 shows an alternative embodiment of the coupling means 500 between the stylet 203 and the guidewire 211. In that embodiment, the stylet 203 has a narrow lumen 507 with a wider inner section 501. The guidewire has a narrow member 503 with a bulb 505 at the end. The narrow member 503 has a smaller diameter than the bulb 505 or the guidewire 211. The guidewire 211 and the bulb 505 may have the same diameter, or they may be different from each other. The length of the narrow member 503 is approximately equivalent to the length of the narrow lumen 507, such that when the coupling section is fully inserted, the bulb 505 sits within the wide inner section 501 and the narrow member 503 sits within the narrow lumen 507. The stylet is made of a resilient material, but that material yields and stretches around the bulb 505 when the bulb 505 is pushed through the narrow lumen 507 by a user. The distal end of the stylet 203 closes back around the narrow member 503 once the bulb 505 has been pushed all the way through. To remove the stylet 203 and guidewire from each other, the user simply pulls them apart. The amount of force required to pull them apart is preferably more than 5 lbs. of force.

Figure 6:
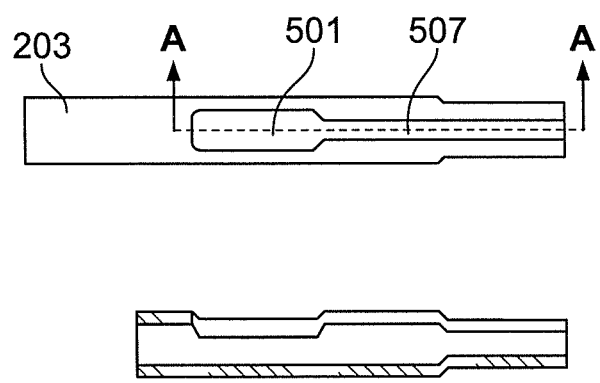
FIG. 6 shows diagrams of cross-sections of the distal end of a stylet, showing the connection mechanism.

FIG. 6 shows cross-sectional views of the distal end of the stylet, as used in the coupling means 500 of FIG. 5. The distal end of the stylet 203 defines a narrow lumen 507 and a wide inner section 501.

Figure 7:
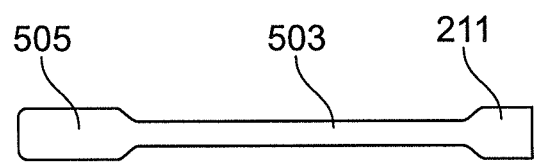
FIG. 7 shows a diagram of the connection mechanism at the proximal end of a guidewire.

FIG. 7 shows a cross-sectional view of the coupling section 213 of the guidewire 211, as shown in FIG. 5. In the embodiment shown, the bulb 505 and the guidewire 211 have the same diameter, whereas the narrow member 503 has a smaller diameter. The coupling section 213 fits within the lumen of the stylet, as described above.

Figure 8:
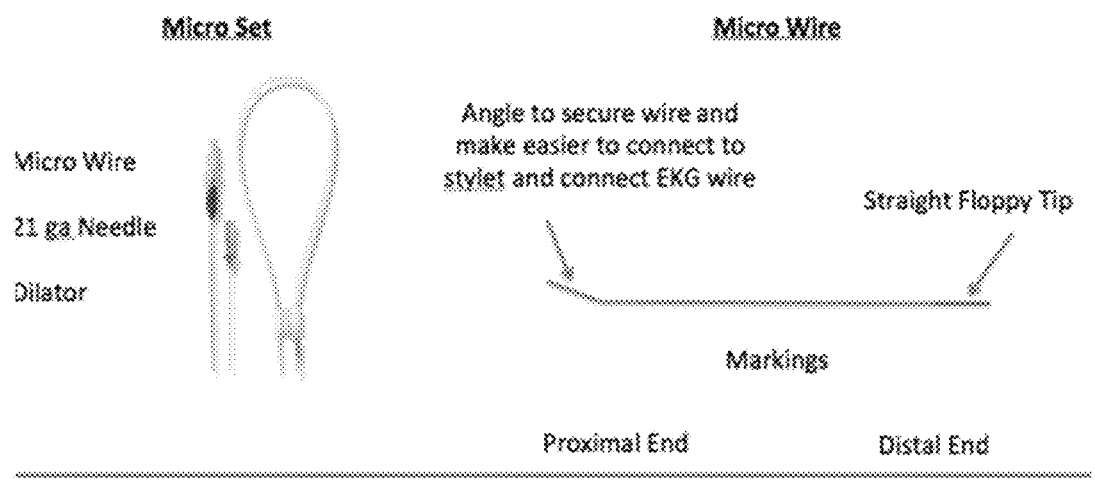
FIG. 8 shows micro wires and a comparison to existing wires.

FIG. 8 shows some guidewires, or "micro wires," for use with the invention. The guidewire can have an angled proximal end to secure the wire and make it easier to connect to the stylet or connect an EKG wire in embodiments where the system is used for EKG. The guidewire can be introduced using a 21 gauge needle or the like. A dilator can be used to dilate the access site as needed. FIG. 8 also includes a table comparing existing guidewire sizes with the smaller guidewire sizes provided by the invention. For example, to insert a 7 Fr×16 cm 3-L catheter, traditional methods require a 0.032-inch guidewire. Using methods of the present disclosure, however, allows that same catheter to be introduced using a 0.018-inch micro wire. The invention allows the use of a smaller guidewire than traditional methods allow.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention may be practiced without one or more of the specific details, or with other methods, components, materials, and so forth. In other instances, well-known structures, materials or operations are not shown or described in detail to avoid obscuring aspects of the invention.

The schematic flow chart diagrams included herein are generally set forth as logical flow chart diagrams. As such, the depicted order and labeled steps are indicative of one embodiment method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed are provided in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

While methods, devices, compositions, and the like, have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims. It is understood that the term, present disclosure, in the context of a description of a component, characteristic, or step, of one particular embodiment of the disclosure, does not imply or mean that all embodiments of the disclosure comprise that particular component, characteristic, or step.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC § 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps. Such terms should be interpreted in their most expansive forms so as to afford the applicant the broadest coverage legally permissible.

What is claimed is:

1. A method for introducing a catheter into a blood vessel, the method comprising:
   inserting a hollow needle into a blood vessel;
   feeding a guidewire through the needle, the guidewire having a proximal end and a distal end;
   removing the needle from the blood vessel; providing a catheter set comprising:
   a catheter having a proximal end and a distal end and defining a lumen; and
   a stylet having a proximal end and a distal end, wherein the stylet is disposed within the catheter lumen, and wherein the distal end of the stylet extends out of the distal end of the catheter;
   connecting the distal end of the stylet to the proximal end of the guidewire to create a stylet-guidewire complex;
   advancing the catheter into the vessel over the stylet-guidewire complex; and withdrawing the stylet-guidewire complex.

2. The method of claim 1, wherein the hollow needle defines a needle lumen extending axially therethrough, and wherein the needle lumen has a diameter greater than a diameter of the stylet.

3. The method of claim 1, wherein the guidewire is between 15 and 20 cm in length, and between 0.018 inches and 0.035 inches in diameter, and wherein the stylet has a diameter equal to or greater than the diameter of the guidewire.

4. The method of claim 1, wherein the guidewire comprises markings to indicate distance inserted.

5. The method of claim 1, wherein the guidewire comprises a J-tip or a floppy tip.

6. The method of claim 1, wherein the stylet extends at least 3 cm past the distal end of the catheter.

7. The method of claim 1, wherein the catheter set further comprises a
   catheter extension line and
   a luer, and wherein the proximal end of the stylet is secured to the luer.

8. The method of claim 7, further comprising disconnecting the proximal end of the stylet from the luer prior to the advancing step.

9. The method of claim 7, wherein the proximal end of the stylet is secured to the luer with a cap.

10. The method of claim 1, wherein the stylet comprises a solid flexible material or a metal coil.

11. The method of claim 1, further comprising flushing the catheter with a fluid prior to the connecting step.

12. A system for introducing a catheter into a blood vessel, the system comprising:
    a catheter having a proximal end and a distal end and defining a lumen;
    a stylet having a proximal end and a distal end, wherein the stylet is disposed within the catheter lumen, and wherein the distal end of the stylet extends out of the distal end of the catheter;
    wherein the distal end of the stylet is configured to be connectable to the proximal end of the guidewire to create a stylet-guidewire complex; and wherein the catheter is configured to be advanceable over the stylet-guidewire complex; and the stylet-guidewire complex is configured to be withdrawn, leaving the catheter in place in the blood vessel, and wherein the guidewire is between 15 and 20 cm in length, and between 0.018 inches and 0.035 inches in diameter, and wherein the stylet has a diameter equal to or greater than the diameter of the guidewire.

13. A system for introducing a catheter into a blood vessel, the system comprising:
   a catheter set comprising:
   a catheter having a proximal end and a distal end and defining a lumen;
   a stylet having a proximal end and a distal end, wherein the stylet is disposed within the catheter lumen, and wherein the distal end of the stylet extends out of the distal end of the catheter;
   wherein the distal end of the stylet is configured to be connectable to the proximal end of the guidewire to create a stylet-guidewire complex;
   wherein the catheter is configured to be advanceable over the stylet-guidewire complex;
   wherein the guidewire comprises a J-tip or a floppy tip and,
   wherein the stylet extends at least 3 cm past the distal end of the catheter.

14. A system for introducing a catheter into a blood vessel, the system comprising:
   a catheter set comprising:
   a catheter having a proximal end and a distal end and defining a lumen;
   a stylet having a proximal end and a distal end, wherein the stylet is disposed within the catheter lumen, and wherein the distal end of the stylet extends out of the distal end of the catheter;
   wherein the distal end of the stylet is configured to be connectable to the proximal end of the guidewire to create a stylet-guidewire complex;
   wherein the catheter is configured to be advanceable over the stylet-guidewire complex;
   wherein the guidewire comprises a J-tip or a floppy tip and
   wherein the stylet extends at least 3 cm past the distal end of the catheter
   wherein the catheter set further comprises a catheter extension line and a luer, and
   wherein the proximal end of the stylet is secured to the luer, wherein the stylet comprises a solid flexible material or a metal coil; and wherein the stylet extends at least 3 cm past the distal end of the catheter; and, wherein the stylet defines a lumen open to the distal end, and wherein proximal end of the guidewire connects to the distal end of the stylet by nesting within the stylet lumen, thereby generating at least 5 lbs. of frictional coupling force.

* * * * *